United States Patent
Sawada (10) Patent No.: US 6,423,087 B1
(45) Date of Patent: Jul. 23, 2002

(54) INTERNAL ORGAN WALLS JOINING INSTRUMENT FOR AN ENDOSCOPE

(75) Inventor: Muneo Sawada, Nara (JP)

(73) Assignee: Olympus Optical Co., Ltd., Tokyo (JP)

( * ) Notice: Subject to any disclaimer, the term of this patent is extended or adjusted under 35 U.S.C. 154(b) by 154 days.

(21) Appl. No.: 09/621,706

(22) Filed: Jul. 21, 2000

(30) Foreign Application Priority Data

Aug. 4, 1999 (JP) .......................................... 11-221488

(51) Int. Cl.[7] .............................................. A61B 17/08
(52) U.S. Cl. ...................... 606/213; 606/216; 606/217; 606/232; 606/151; 606/153; 606/157
(58) Field of Search ........................... 606/1, 139, 200, 606/213, 215, 157, 8, 216, 217, 232, 151, 153, 156; 623/11

(56) References Cited

U.S. PATENT DOCUMENTS

| | | | | |
|---|---|---|---|---|
| 4,235,238 A | * | 11/1980 | Ogiu et al. .................. | 606/145 |
| 4,669,473 A | * | 6/1987 | Richards et al. ............ | 606/215 |
| 5,041,129 A | * | 8/1991 | Hayhurst et al. ........... | 606/139 |
| 5,052,998 A | | 10/1991 | Zimmon | |
| 5,108,420 A | * | 4/1992 | Marks ........................ | 606/151 |
| 5,176,626 A | | 1/1993 | Soehendra | |
| 5,306,301 A | * | 4/1994 | Graf et al. .................. | 606/151 |
| 5,364,407 A | * | 11/1994 | Poll .......................... | 24/136 R |
| 5,662,681 A | * | 9/1997 | Nash et al. ................. | 604/285 |
| 5,728,114 A | * | 3/1998 | Evans et al. ................ | 128/887 |
| 5,728,122 A | * | 3/1998 | Leschinsky et al. ........ | 604/526 |
| 5,800,507 A | | 9/1998 | Schwartz | |
| 5,810,848 A | * | 9/1998 | Hayhurst .................... | 606/139 |
| 5,849,034 A | | 12/1998 | Schwartz | |
| 5,861,003 A | * | 1/1999 | Latson et al. ............... | 606/157 |
| 5,868,754 A | * | 2/1999 | Levine et al. ............... | 606/1 |
| 5,916,236 A | | 6/1999 | Muijs Van der Moer et al. | |
| 5,935,147 A | | 8/1999 | Kensey et al. | |
| 5,957,971 A | | 9/1999 | Schwartz | |
| 5,976,158 A | * | 11/1999 | Adams et al. ............... | 606/140 |
| 6,033,427 A | * | 3/2000 | Lee ............................ | 604/15 |
| 6,059,816 A | * | 5/2000 | Moenning .............. | 604/164.01 |
| 6,071,292 A | * | 6/2000 | Makower et al. ........... | 606/139 |
| 6,074,409 A | * | 6/2000 | Goldfarb .................... | 606/151 |
| 6,110,207 A | * | 8/2000 | Eichhorn et al. ........... | 606/232 |
| 6,120,525 A | * | 9/2000 | Westcott .................... | 606/216 |
| 6,162,240 A | * | 12/2000 | Cates et al. ................. | 606/213 |

FOREIGN PATENT DOCUMENTS

| | | |
|---|---|---|
| EP | 0606165 A1 | 7/1994 |
| EP | 0824903 A1 | 2/1998 |
| JP | 6-7455 | 1/1994 |
| JP | 6-292730 | 10/1994 |
| JP | 10-174720 | 6/1998 |

* cited by examiner

Primary Examiner—Michael J. Milano
Assistant Examiner—Daniel Jacal Davis
(74) Attorney, Agent, or Firm—Kenyon & Kenyon (57) ABSTRACT

An internal organ walls joining instrument for an endoscope is used for endoscopically joining two internal organ walls spaced apart from each other, and for endoscopically forming a fistula between the two internal organ walls. The instrument has at least a first stationary part, a second stationary part, a first line member, a second line member, and a stopper. Each of the first and the second line members is respectively coupled to the first stationary part, the second stationary part, and the stopper. The two internal organ walls are pinched between the first stationary part and the second stationary. The stopper keeps the two internal organ walls in the pinched state. In this state, the fistula is made by an electro-knife. The instrument remains for a certain time until fistula becomes strong, after which it is endoscopically removed.

7 Claims, 6 Drawing Sheets

FIG. 1

Fig. 2 proximal side

INTERNAL ORGAN WALLS JOINING INSTRUMENT FOR AN ENDOSCOPE

CROSS REFERENCE TO RELATED APPLICATION

This application is based on and claims priority of Japanese Patent Application No. Hei 11-221488 filed on Aug. 9, 1999, the content of which is incorporated herein by reference.

BACKGROUND OF THE INVENTION

1. Field of the Invention

The present invention relates to an instrument, for use with an endoscope to join walls of internal organs endoscopically.

2. Description of the Related Art

Traditionally, a percutaneous transhepatic cholangio drainage (PTBD) is used in an operation for a jaundice, which a part of a bile duct of a human being, that is closed by a lesion.

Recently, technology of the endoscope has progressed, so that endoscopic retrograde biliory drainage (ERBD) and endoscopic bilionasal drainage (ENBD) may be used for an operation for a closed jaundice.

The ERBD is a procedure to perorally insert an endoscope, and to insert a tubular stent tube inside the body through a channel of the endoscope. The tube is kept inside the body to open the closed bile duct and enable the drainage of bile.

A conventional stent for the inner-body is disclosed in, for example, Japanese Laid-Open Patent Publication Nos. Hei 6-7455, Hei 6-292730, and Hei 10-174720.

Japanese Laid-Open Patent Publication No. Hei 6-7455 discloses a stent for the lumen including cellulose to cure a return of a stricture, and a method for producing the stent. The stent can be supplied to a portion of a stoppage or a stricture by means of a catheter.

Japanese Laid-Open Patent Publication No. Hei 6-292730 discloses a stent comprises a hollow tube which has openings at both end portions thereof, and which has a series of slots. The stent expands an internal passage by inelastic deformation. The slots of its end portions are rounded so that they do not hurt the internal passage.

Japanese Laid-Open Patent Publication No. Hei 10-174720 discloses a stent processed to have an outline to help keep an opening of the lumen. The stent has at least one support which has a first plane, a second plane, a third plane, and three rounded edges which are formed at a position where the first, second, and third plane meet, so that the stent does not hurt the lumen.

However, a conventional stent tube is composed of synthetic resin, so constituents of bile adhere to the inside of the stent tube, and the stent tube starts to thin down as time passes. Eventually, the constituents of the bile close the stent tube.

In a case where the stent tube has become closed, a procedure is needed to remove the stent tube, and replace the old stent with a new one using the endoscope.

That is, an endoscope procedure is required whenever the constituents of the bile close the stent tube. This problem troubles a patient.

BRIEF SUMMARY OF THE INVENTION

The present invention made in consideration of the above mentioned problems is intended to provide an internal organ walls joining instrument comprises a first stationary part, a second stationary part, a first line member having a free end portion, a second line member, a stopper disposed between the free end portion of the first line member and the first stationary part such that the stopper can be moved along the first line member and kept at a certain position on the first line member, wherein the free end portion of the first line member passes through a through hole, which is formed in substantially the middle of a longitudinal direction of the first stationary part and is perpendicular to a longitudinal direction of the first stationary part, another end portion of the first line member is fixed to substantially the middle of a longitudinal direction of the second stationary part, one end portion of the second line member is fixed to an end portion of a longitudinal direction of the second stationary part, and another end portion of the second line member is coupled to an end portion of a longitudinal direction of the first stationary part.

BRIEF DESCRIPTION OF THE DRAWINGS

The accompanying drawings, which are incorporated in and constitute a part of the specification, illustrate exemplary embodiments of the invention, and together with the general description above and the detailed description of the preferred embodiments given below, serve to explain the principles of the invention.

DETAILED DESCRIPTION

First Embodiment

Referring to the drawings, a first embodiment of the present invention will be described.

Figure 1:
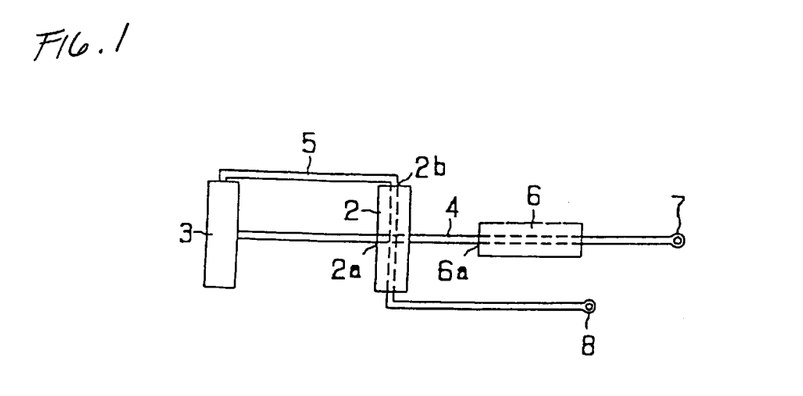
FIG. 1 shows the structure of an instrument, for use with an endoscope, in joining internal organ walls, according to a first embodiment of the invention.

FIG. 1 shows the structure of an instrument, for use with an endoscope, in joining internal organ walls, according to a first embodiment of the invention. In describing this embodiment, joining a wall of a duodenum and a wall of a hepatic duct will be described. By using this internal organ walls joining instrument, for example, a procedure to endoscopically form a fistula to connect the duodenum and the hepatic duct is possible.

In FIG. 1, the internal organ walls joining instrument 1 for an endoscope comprises a first cylindrical stationary part 2, a second cylindrical stationary part 3, an operating lanyard 4 forming a first line member, an operating lanyard 5 forming a second line member, and a stopper 6.

For example, the stationary parts 2 and 3 are formed by cylindrical insulating materials composed of synthetic resin or ceramic. Furthermore, a X-ray contrast medium is added to the stationary part 2, the stationary part 3, and the stopper 6.

The diameters of the stationary part 2, the stationary part 3, and the stopper 6 are about 2 mm in this embodiment. These diameters are smaller than an inner diameter of an outer tube 12 as explained below (see FIG. 2). The length of each of the stationary parts 2 and 3 is 15 mm in this embodiment.

The operating lanyards 4 and 5 are line members composed of flexible synthetic resin. One end portion of the operating lanyard 4 is fixed close to the middle of a longitudinal direction of the stationary part 3, and the other end portion of the operating lanyard 4 is free. The operating lanyard 4 passes through a through hole 2a formed close to the middle of a longitudinal direction of the stationary part 2, and passes through a through hole 6a formed in the stopper 6. The free end portion of the operating lanyard 4 has a loop 7 to enable to be held by a hook 19 as explained below (see FIG. 3). Also, for example, a round shape would be a good shape as the free end portion if it were easy to be held by the hook 19 or something like that.

One end portion of the operating lanyard 5 is fixed to an end portion of the stationary part 3, the other end portion of the operating lanyard 5 is free. The operating lanyard 5 passes through a through hole 2b formed in a longitudinal direction of the stationary part 2. The free end portion of the operating lanyard 5 has a loop 8 similar to the loop 7.

The stopper 6 is a tubular member composed of an elastic material such as a silicone rubber. The inner diameter of the stopper 6 is smaller than an outer diameter of the operating lanyard 4. An outer diameter of the stopper 6 is bigger than a diameter of the through hole 2a. Also, the outer diameter of the stopper 6 is bigger than an inner diameter of an inner tube 13 as explained below (see FIG. 2).

In addition, the length of each of the operating lanyards 4 and 5 between stationary parts 2 and 3 is equal to the length between the wall of the duodenum and the wall of the hepatic duct. Furthermore, the operating lanyard 4 has enough length that the stationary part 2 can change its position when the stationary part 2 is pushed out of the outer tube 12 (see FIG. 2) in a series of indwelling procedures as explained below (see FIGS. 9 and 10).

Figure 2:
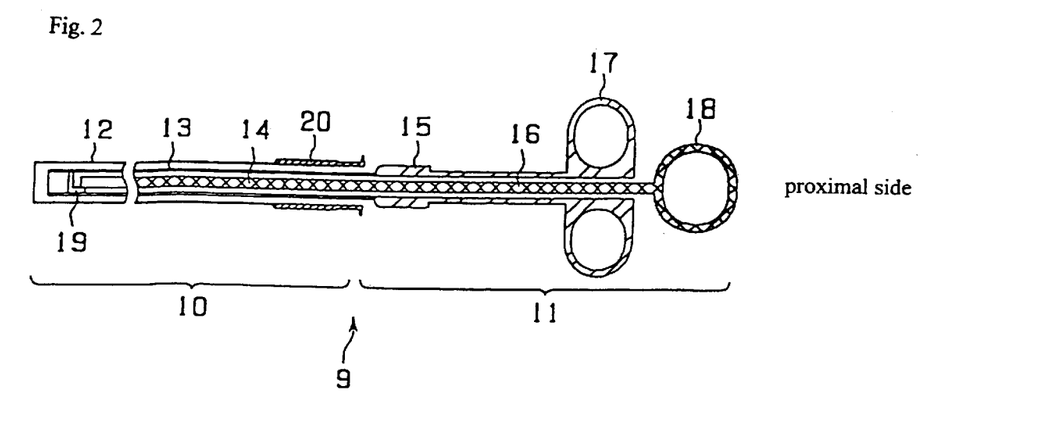
FIG. 2 shows a sectional view of an indwelling device to carry the internal organ walls joining instrument to the inside of the body, and keep instrument inside the body.

FIG. 2 shows an indwelling device 9 to carry the internal organ walls joining instrument 1 to the inside of the body, and keep the internal organ walls joining instrument 1 inside the body.

The indwelling device 9 in FIG. 2 comprises an inserting part 10 and a handling part 11.

The inserting part 10 has an outer tube 12 acting as a guiding member, an inner tube 13 acting as a moving member for the stopper 6, and a pull wire 14 forming a holding member.

The handling part 11 has a body 15 of a handle, a sliding portion 16, a handhold 17 articulated to the body 15, and a handhold 18 articulated to the sliding portion 16.

The outer tube 12 is a flexible tube, and has a socket 20 at a proximal portion thereof. The outer diameter of the outer tube has a dimension that enables inserting the endoscope into a channel.

The inner tube 13 is a flexible tube. The inner tube 13 is movably inserted into the outer tube 12. A proximal portion of the inner tube 13 is fixed to the body 15.

The pull wire 14 is a flexible tube. The pull wire 14 is movably inserted into the inner tube 13. The pull wire 14 has a hook 19 at a distal portion thereof; a proximal portion of the pull wire 14 is fixed to the sliding portion 16.

The sliding portion 16 is disposed in the body 15. The sliding portion 16 is built into the body 15, and is able to move back and forth relative to the body 15.

The handhold 17 is fixed to a proximal portion of the body 15. The handhold 18 is fixed to a proximal portion of the sliding portion 16.

Figure 3:
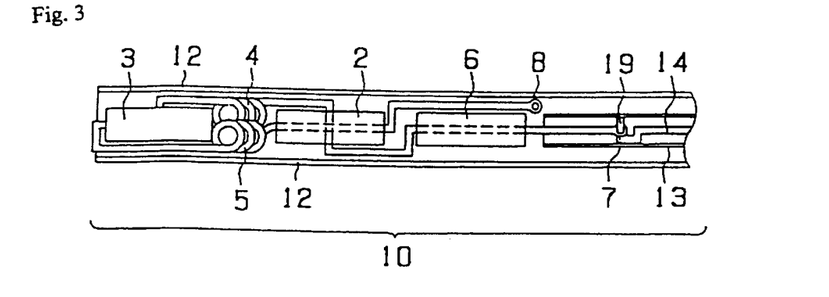
FIG. 3 shows a sectional view of a distal portion of an insert section of the indwelling device with the internal organ walls joining instrument.

FIG. 3 shows a state in which the internal organ walls joining instrument 1 is loaded into the inserting part 10 of the indwelling device 9.

Figure 4:
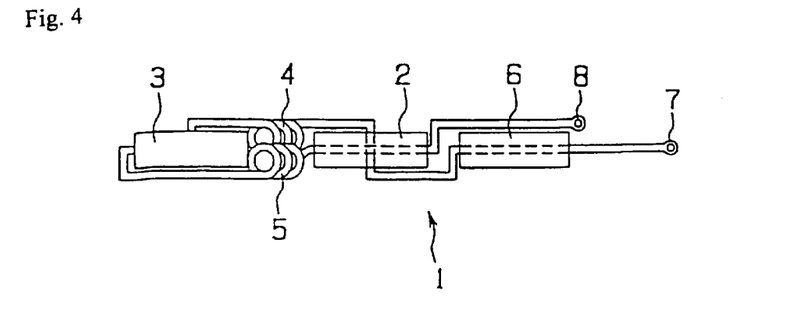
FIG. 4 shows an arrangement of the internal organ walls joining instrument, which is loaded in the indwelling device.

As shown in FIG. 3, the internal organ walls joining instrument 1 is loaded into the inside of the end portion of the outer tube 12 in a state that the handhold 17 is retracted to the right in FIG. 2 so that a tip of the inner tube 13 is retracted inside the end portion of the outer tube 12. The loop 7 is hooked to the hook 19 fixed to the tip of the pull wire 14 disposed inside the inner tube 13. In this situation, the internal organ walls joining instrument is arranged inside the end portion of the outer tube 12 as shown in FIG. 4.

Each of the operating lanyards 4 and 5 has a spiral part so as to have a margin for the length.

Following is a description of the functioning of this embodiment.

The endoscope (not shown) is perorally inserted inside the body so that the end portion of the endoscope is led to a duodenum. The end portion of the endoscope is positioned at a point where the distance between the duodenum and the hepatic duct becomes a minimum, using an ultrasonic diagnostic apparatus, X-ray apparatus and so on.

In the case where an ultrasonic endoscope is used, it is comparatively easy to locate the end portion of the endoscope at a predetermined point because an ultrasonic sectional image is obtained with the ultrasonic endoscope. As mentioned above, an X-ray contrast medium is added to the stationary part 2, the stationary part 3, and the stopper 6, so that the position of the end portion of the endoscope can be clearly determined.

A puncture needle or an electro-knife is inserted inside the body through the channel of the endoscope so as to puncture from the duodenum 22 to the hepatic duct 21. A hole punctured by the puncture needle or the electro-knife is numbered 23 in FIG. 5.

Figure 5:
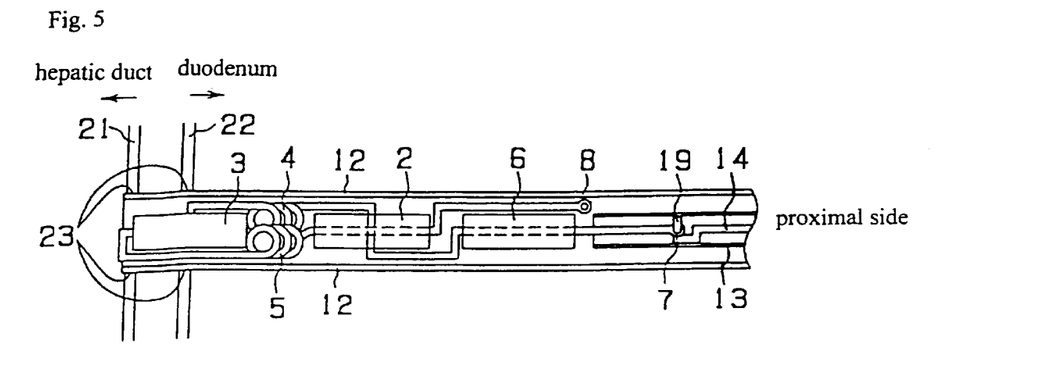
FIG. 5 shows a sectional view of a step in a procedure to carry the internal organ walls joining instrument to the inside of the body, and keep the internal organ walls joining instrument inside the body.

The hole 23 is a temporary hole to insert the internal organ walls joining instrument 1 inside the body, and join the wall of the duodenum and the wall of the hepatic duct.

Next, in the state of FIG. 3, the state in which the internal organ walls joining instrument 1 is built into the inserting part 10 of the indwelling device 9, the inserting part 10 is inserted into the channel of the endoscope (not shown). At this point, the handling part 11 is arranged outside the channel of the endoscope.

Following is an explanation, referring to the drawings (FIGS. 5–17), of a series of steps of a procedure to join the wall of the duodenum and the wall of the hepatic duct by using the internal organ walls joining instrument 1 and the indwelling device 9. The series of steps includes keeping the internal organ walls joining instrument 1 inside the body, and removing the stitches from the wound, and the procedures to finally form a fistula to connect the duodenum and the hepatic duct.

The inserting part 10 of the indwelling device 9 is inserted through the channel of the endoscope (not shown) by handling the handling part 11 and the socket 20 (see FIG. 2) of the outer tube 12. Then, as shown in FIG. 5, the tip of the outer tube 12 is inserted into the hole 23. Finally, a certain length of the outer tube 12 is inserted into the hepatic duct 21.

Figure 6:
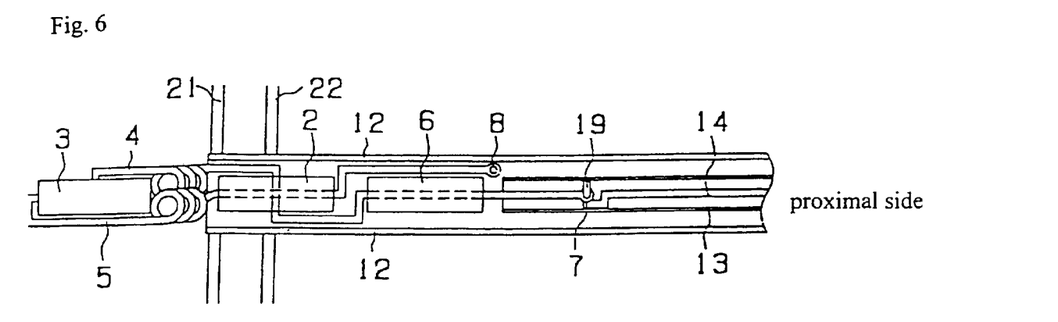
FIG. 6 shows a sectional view of a step in the procedure to carry the internal organ walls joining instrument to the inside of the body, and keep the internal organ walls joining instrument inside the body.

The body 15 (see FIG. 2) is advanced so as to move the inner tube 13 inside the outer tube 12 as shown in FIG. 6. Then the stationary part 3 disposed at the tip of the inner tube 13 is pushed out of the outer tube 12 by the inner tube 13.

Figure 7:
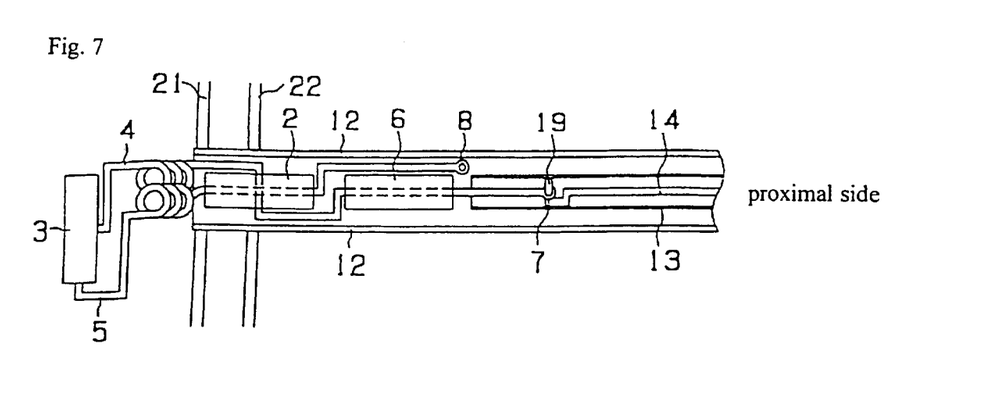
FIG. 7 shows a sectional view of a step in the procedure to carry the internal organ walls joining instrument to the inside of the body, and keep the internal organ walls joining instrument inside the body.

As mentioned above, the operating lanyards 4 and 5 between the stationary part 2 and the stationary part 3 have a margin, formed by a spiral part, for the length to change the position of the stationary part 3. So the position of the stationary part 3 can be changed after the stationary part 3 is pushed out of the outer tube 12 as shown in FIG. 7.

Figure 8:
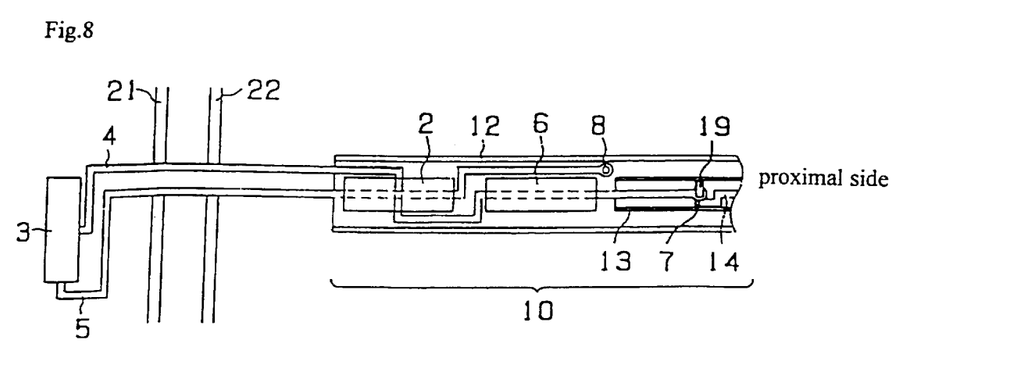
FIG. 8 shows a sectional view of a step in the procedure to carry the internal organ walls joining instrument to the inside of the body, and keep the internal organ walls joining instrument inside the body.

Then, the outer tube 12 and the handling part 11 are pulled back so that the tip of the inserting part 10 is pulled back from the side of the wall of the duodenum 22 as shown in FIG. 8.

Figure 9:
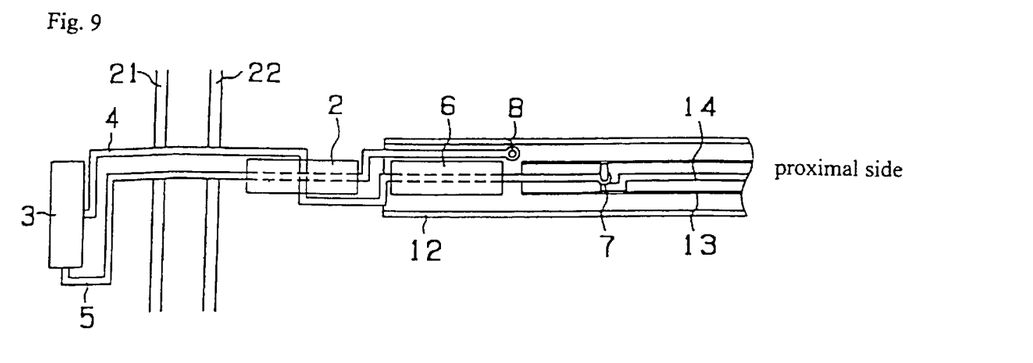
FIG. 9 shows a sectional view of a step in the procedure to carry the internal organ walls joining instrument to the inside of the body, and keep the internal organ walls joining instrument inside the body.

The body 15 is moved so as to move the inner tube 13 to a position where the tip of the inserting part 10 is pulled back from the side of the wall of the duodenum 22. Then the stationary part 2 of the internal organ walls joining instrument 1 is pushed out of the outer tube 12 by the inner tube 13 as shown in FIG. 9.

Figure 10:
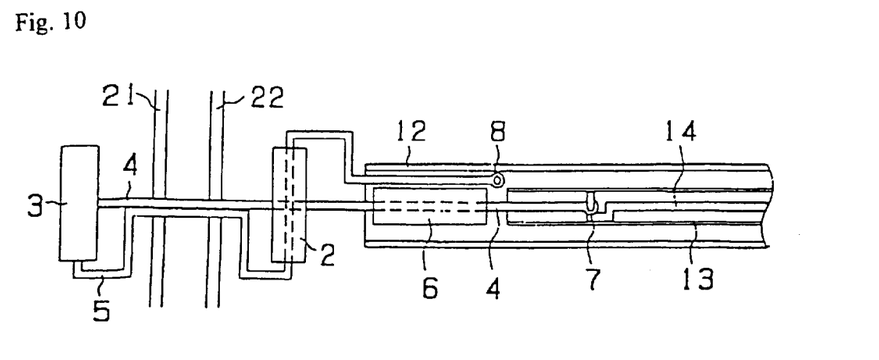
FIG. 10 shows a sectional view of a step in the procedure to carry the internal organ walls joining instrument to the inside of the body, and keep the internal organ walls joining instrument inside the body.

Next, the handhold 18 is pulled back in the direction of the near hand side so as to pull the pull wire 14 into the inner tube 13, and pull the operating lanyard 4 as shown in FIG. 10.

Figure 11:
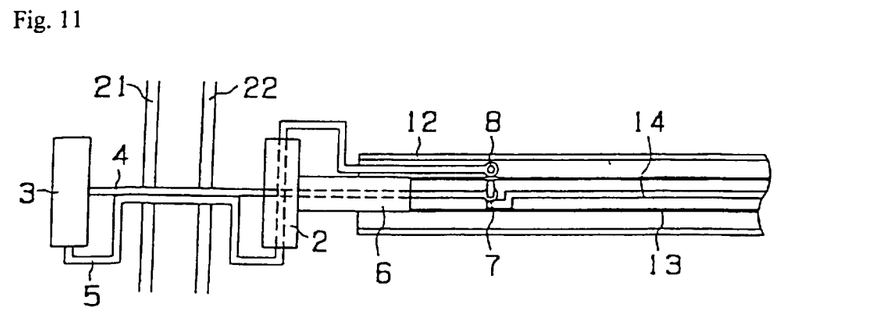
FIG. 11 shows a sectional view of a step in the procedure to carry the internal organ walls joining instrument to the inside of the body, and keep the internal organ walls joining instrument inside the body.
Figure 12:
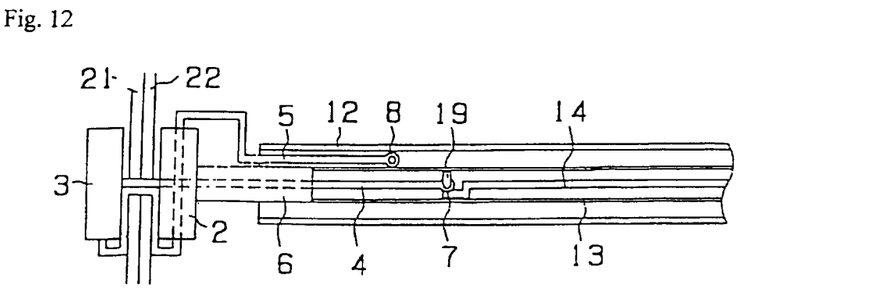
FIG. 12 shows a sectional view of a step in the procedure to carry the internal organ walls joining instrument to the inside of the body, and keep the internal organ walls joining instrument inside the body.

At this point, an end portion of the stopper 6 is in contact with an end portion of the inner tube 13 as shown in FIG. 11. Furthermore, the pull wire 14 is pulled into the inner tube 13, so that the walls of the each of duodenum 22 and the hepatic duct 21 are pulled together, and held in contact by means of the stationary parts 2 and 3 as shown in FIG. 12.

Figure 13:
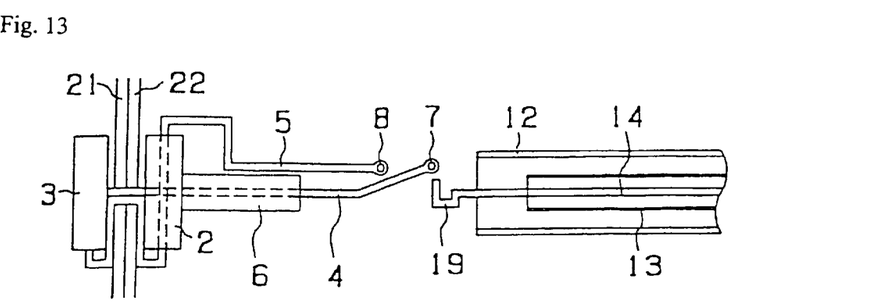
FIG. 13 shows a sectional view of a step in the procedure to carry the internal organ walls joining instrument to the inside of the body, and keep the internal organ walls joining instrument inside the body.

Next, the socket 20, the outer tube 12, the body 15 and the inner tube 13 are pulled back so as to relatively move the sliding portion 16 and the pull wire 14. As a result, the hook 19 moves out of the end portions of the inner tube 13 and the outer tube 12, and an engagement between the hook 19 and loop 7 is released as shown in FIG. 13. Then, the internal organ walls joining instrument is kept inside the body in the state where the internal organ walls joining instrument holds the walls of the duodenum 22 and the hepatic duct 21 together by means of the frictional force between the stopper 6 and the operating lanyard 4 as shown in FIG. 14.

The same procedure as mentioned above can be carried out wherever it is needed.

Figure 14:
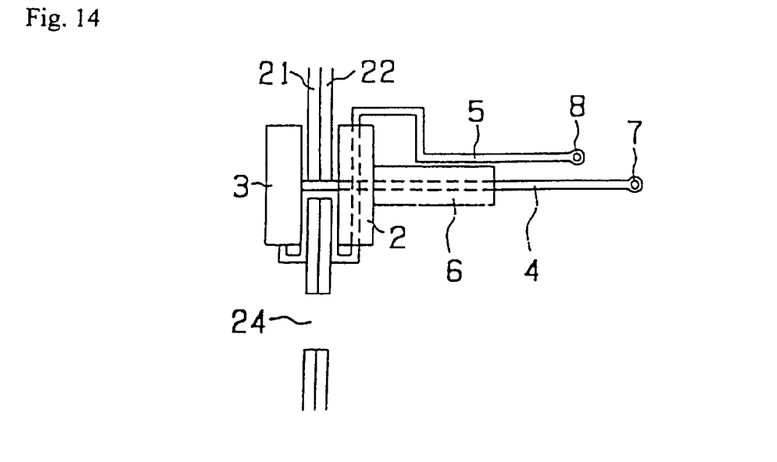
FIG. 14 shows a step in a procedure to remove the internal organ walls joining instrument.

Next, an electro-knife is inserted through the channel of the endoscope (not shown) so as to form a hole (a fistula) 24 near the point where the two walls are held together, to connect the duodenum 22 and the hepatic duct 21 (see FIG. 14). In this embodiment, all parts of the internal organ walls joining instrument 1 are made with insulating materials. So there is no current-carrying part if any electro-knives are used.

After the above procedure, the members holding the two walls together are left in for sufficient time for the hole (the fistula) 24 becomes strong.

After the hole (the fistula) 24 has become strong, the internal organ walls joining instrument is not needed any longer. Accordingly, the following procedure will be done to remove the internal organ walls joining instrument.

Figure 15:
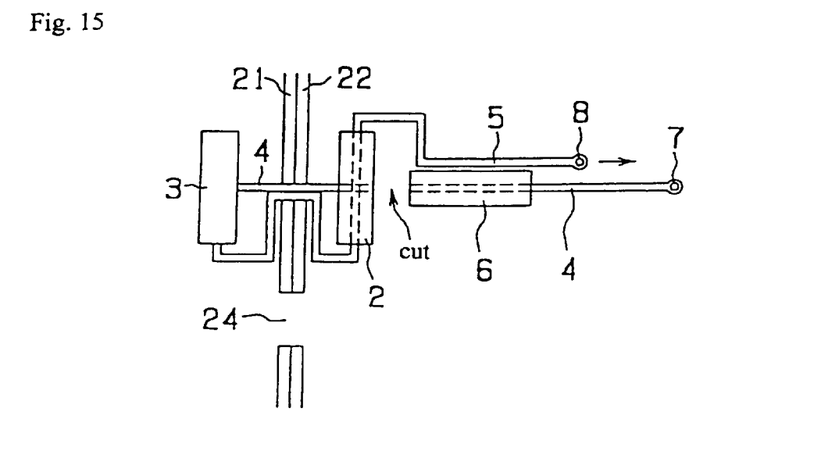
FIG. 15 shows the procedure to remove the internal organ walls joining instrument.

Forceps (not shown) with scissors are inserted through the channel of the endoscope (not shown) so as to cut the operating lanyard 4 between the stopper 6 and the stationary part 2 as shown in FIG. 15. Recovery of the stopper 6 and the operating lanyard 4 is carried out by means of forceps (not shown) with a holding part.

Figure 16:
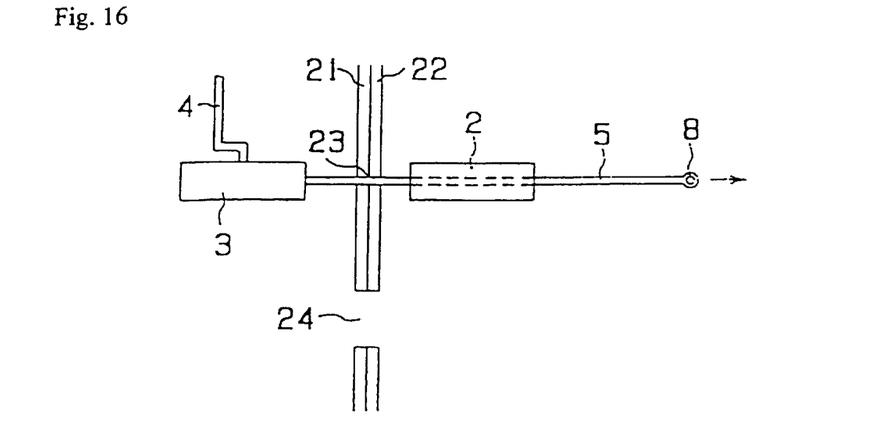
FIG. 16 shows a step in the procedure to remove the internal organ walls joining instrument.
Figure 17:
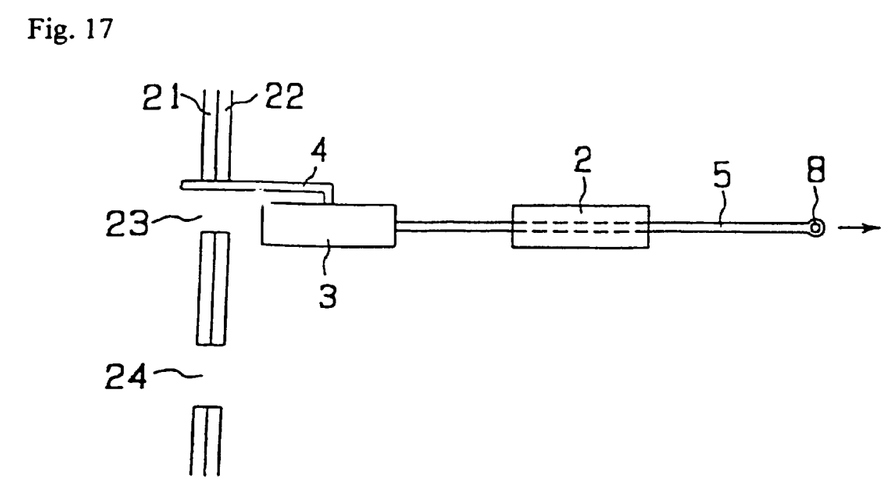
FIG. 17 shows a step in the procedure to remove the internal organ walls joining instrument.

Next, the loop 8 is pulled back. Then an engagement between the stationary part 2 and the operating lanyard 4 is released, and the operating lanyard 5 is pulled back toward the near hand direction. As a result, the stationary part 3 changes its direction such that the longitudinal direction of the stationary part 3 is substantially perpendicular to the wall of the hepatic duct 21 as shown in FIG. 16. Accordingly, all parts of the wall-joining instrument 1 can be removed because it becomes easy for the stationary part 3 passes through the hole 23.

According to the first embodiment as explained above, it becomes possible to join walls spaced apart from each other, for example, the walls of the duodenum 22 and the hepatic duct 21, by endoscopically using the internal organ walls joining instrument 1 as shown in FIG. 1 and the indwelling device 2 as shown in FIG. 2. Accordingly, it becomes easy to form a fistula between the duodenum and the hepatic duct. Furthermore, after forming the fistula, nothing is left inside the body because all parts of the wall-joining instrument can be absolutely removed.

Second Embodiment

Figure 18:
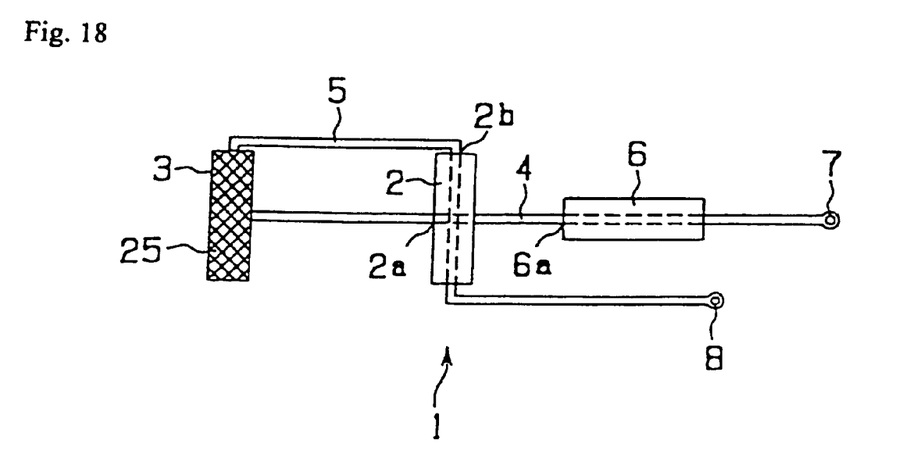
FIG. 18 shows a structure of internal organ walls joining instrument for an endoscope according to the second embodiment of the invention.

FIG. 18 shows a structure of an internal organ walls joining instrument for an endoscope according to a second embodiment of the present invention.

In the second embodiment shown in FIG. 18, a plurality of mesh-like dimples, a fine uneven pattern 25, are formed on a surface of the stationary part 3, described above in connection with the first embodiment, by a marking procedure using a laser beam. These dimples reinforce ultrasonic echoes, i.e, ultrasonic reflection from the stationary part 3, of an ultrasonic diagnostic apparatus which is employed to locate part 3. Any kind of dimples including figures and/or patterns can be used to reinforce ultrasonic echoes of an ultrasonic diagnostic apparatus.

The functioning of the second embodiment is the same as the one of the first embodiment. In the second embodiment, the stationary part 3 can be moved into place while it is displayed on a monitor as an ultrasonic image. In this case, there is an advantage of control of the internal organ walls joining instrument 1 inside the body under the guide of the ultrasonic image. Otherwise, the second embodiment has the same advantages that the first embodiment has.

Incidentally, in the internal organ walls joining instrument as shown in FIG. 1, one end portion of the operating lanyard 5 acting as a second line member is joined to one end portion of the longitudinal direction of the stationary part 3 forming the second cylindrical member. Then, another end portion of the operating lanyard 5 has a loop 8, and passes through the through hole 2b formed in the longitudinal direction of the stationary part 2 forming the first cylindrical member. Furthermore, in the present invention, it is possible to make the following modification on the operating lanyard 5. One end portion of the operating lanyard 5 is fixed to one end portion of the longitudinal direction of the stationary part 3. Then, another end portion of the operating lanyard 5 is fixed (coupled) to one end portion of the longitudinal direction of the stationary part 2. This modification permits that each of the stationary parts 2 and 3 need not be only a cylindrical member but that it can be a stick, bar, rod and so on. That is, the cylindrical shape of the stationary part is not important, but the function explained in connection with the first and the second embodiments is.

By use of the structures in the first and the second embodiment, the fistula can be safely formed to establish a connection between the two internal organs, for example between the duodenum and the hepatic duct. Then, the fistula is unlikely to be closed by the constituents of the bile because the formed fistula is a part of a living body. Accordingly, the burden of patients, who otherwise would have to change a stent tube whenever the constituents of the bile close the stent tube, can be eliminated.

What is claimed is:

1. An internal organ wall joining instrument comprising:
   a first stationary part;
   a second stationary part;
   a first line member having a free end portion;
   a second line member;
   a stopper disposed between the free end portion of the first line member and the first stationary part such that the stopper can be moved along the first line member and kept at a certain position on the first line member;
   wherein the free end portion of the first line member passes through a through hole, which is formed in substantially the middle of a longitudinal direction of the first stationary part and is perpendicular to a longitudinal direction of the first stationary part,
   another end portion of the first line member is fixed to substantially the middle of a longitudinal direction of the second stationary part,
   one end portion of the second line member is fixed to an end portion of a longitudinal direction of the second stationary part, and
   another end portion of the second line member is coupled to an end portion of a longitudinal direction of the first stationary part.

2. The instrument according to claim 1, wherein the first line member has a loop at the free end portion,
   the second line member passes through a through hole formed in a longitudinal direction of the first stationary part, and
   the second line member has a loop at a free end portion thereof.

3. The instrument according to claim 1, wherein an inner diameter of the stopper is smaller than an outer diameter of the first line member, the stopper is a tubular elastic material, and the stopper can not pass through the through hole of the first stationary part.

4. The instrument according to claim 1, wherein at least the second stationary part has a fine uneven pattern thereon so as to reinforce ultrasonic reflection.

5. The instrument according to claim 1, wherein all components of this instrument are made of insulating materials.

6. The instrument according to claim 1, further comprising:
   a guide member;
   an actuator arranged inside of the guide member;
   a hook for holding the free end portion of the first line member; and
   the first stationary part, the second stationary part, the stopper, and the hook disposed inside the guide member.

7. The instrument according to claim 1, wherein at least one of the first and the second stationary parts is a cylindrical member.

* * * * *

UNITED STATES PATENT AND TRADEMARK OFFICE
CERTIFICATE OF CORRECTION

PATENT NO.     : 6,423,087 B1
DATED          : July 23, 2002
INVENTOR(S)    : Muneo Sawada It is certified that error appears in the above-identified patent and that said Letters Patent is hereby corrected as shown below:

<u>Column 1,</u>
Line 7, change "Aug. 9" to -- Aug. 4 --.

Signed and Sealed this

Sixteenth Day of September, 2003

JAMES E. ROGAN
*Director of the United States Patent and Trademark Office*